(12) United States Patent
Ichinose et al.

(10) Patent No.: US 9,072,695 B2
(45) Date of Patent: Jul. 7, 2015

(54) AROMATASE ACTIVATOR

(75) Inventors: Susumu Ichinose, Utsunomiya (JP); Shingo Kakuo, Utsunomiya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/981,994

(22) PCT Filed: Jan. 27, 2012

(86) PCT No.: PCT/JP2012/051745
§ 371 (c)(1),
(2), (4) Date: Jul. 26, 2013

(87) PCT Pub. No.: WO2012/102361
PCT Pub. Date: Aug. 2, 2012

(65) Prior Publication Data
US 2013/0310463 A1 Nov. 21, 2013

(30) Foreign Application Priority Data

Jan. 28, 2011 (JP) ................. 2011-015967

(51) Int. Cl.
*A61K 31/11* (2006.01)
*A61K 8/34* (2006.01)
*A61Q 19/00* (2006.01)
*A61Q 19/08* (2006.01)

(52) U.S. Cl.
CPC ............. *A61K 31/11* (2013.01); *A61K 8/345* (2013.01); *A61K 2800/78* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| 2006/0127412 A1 | 6/2006 | Kakuo et al. |
| 2011/0151036 A1 | 6/2011 | Kakuo et al. |

FOREIGN PATENT DOCUMENTS

| EP | 0 993 822 A1 | 4/2000 | |
| EP | 1 604 676 A2 | 12/2005 | |
| JP | 2000-169359 A | 6/2000 | |
| JP | 2005-343872 A | 12/2005 | |
| JP | 2005-343873 A | 12/2005 | |
| WO | WO 9736604 A1 * | 10/1997 | ............. A61K 35/78 |

OTHER PUBLICATIONS

Machine Translation of WIPO Patent Publication No. 97/36604 A1 (Oct. 2014).*

International Search Report (ISR) for PCT/JP2012/051745; I.A. fd: Jan. 27, 2012, mailed Feb. 28, 2012 from the Japanese Patent Office, Tokyo, Japan.
International Preliminary Report on Patentability (IPRP), Chapter I of the Patent Cooperation Treaty, including the Written Opinion for PCT/JP2012/051745; I.A. fd: Jan. 27, 2012, issued Jul. 30, 2013, by the International Bureau of WIPO, Geneva, Switzerland.
Marner, F-J et al., "Irigermanal and iridogermanal: two new triterpenoids from rhizomes of *Iris germanica* L.," J. Org. Chem. 47:2531-2536 (1982), American Chemical Society, Columbus, OH.
Bonfils, J-P et al., "Cytoptoxicity of iridals, triterpenoids from *Iris*, on human tumor cell lines A2780 and K562," Planta Med. 67(1): 79-81, (Feb. 2001), George Thieme Verlag, Stuttgart, Germany.
Muto, Y et al., "[Studies on antiulcer agents. I. The effects of various methanol and aqueous extracts of crude drugs on antiulcer activity]," J. Pharmaceutical Society of Japan (Yakugaku Zasshi), 114(12): 980-994, (Dec. 1994), Nihon Yakugakkai, Tokyo, Japan.
Lamshoft M et al, "Analysis of the iridals in rhizome extracts of *Iris variegata* Linn," Nat Prod Res, Jan. 2005; 19(1): 57-60; Informa Healthcare, London, England.
Extended European Search Report for EP Application No. 12739254,6, dated Mar. 2, 2015, European Patent Office, Munich, Germany.
Miyake, Y et al., "Identification of iridals as piscicidal components of Iridaceous plants and their conformation associated with CD spectra," Canadian J. Chemistry 75:734-741 (1997), National Research Council, Ottawa, Canada.

* cited by examiner

*Primary Examiner* — Theodore R West
(74) *Attorney, Agent, or Firm* — Sterne, Kessler, Goldstein & Fox P.L.L.C.

(57) ABSTRACT

Provided is a material safely promoting the production of estrogen in a living body. The invention relates to use of a compound represented by the following formula (I) or a solvate thereof for producing an aromatase activator. The invention relates to an aromatase activation method comprising administering a compound represented by the following formula (I) or a solvate thereof (wherein the dashed line indicates that the bond may be a double bond, provided that a and b in the formula (I) do not simultaneously represent a double bond).

(I)

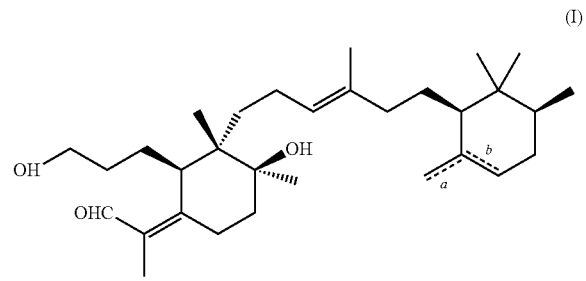

14 Claims, No Drawings

AROMATASE ACTIVATOR

FIELD OF THE INVENTION

The present invention relates to an aromatase activator potentiating the activity of aromatase which is an enzyme biosynthesizing estrogen from androgen.

BACKGROUND OF THE INVENTION

Estrogen in humans is produced primarily in the ovary and acts as female hormone in the body. For example, 17β-estradiol, estrone, and estriol are known as estrogen.

Estrogen participates in various physiological functions such as the proliferation of uterine mucosa, regulation of a sexual function, regulation of hone metabolism, and regulation of lipid metabolism. When estrogen in the body fails along with aging and ovary dysfunction, this causes the occurrence of symptom such as a menopausal disorder, sexual dysfunction, autonomic imbalance, lipid metabolism disorder, vasomotor dysfunction, and osteoporosis.

Therefore, an attempt at hormone replacement therapy has been made to improve the above symptoms. However, it is not easy to externally administer an adequate dose of hormone drugs depending on these symptoms. Furthermore it is known that direct administration of estrogen or estrogen-like substances is accompanied by risks of various side effects such as breast cancer and uterine cancer. It is desired to develop a method for compensating estrogen deficiency in a mild and safe manner like inborn secretion of hormones.

Aromatase is an estrogen-synthesizing enzyme having the effect of converting androgen produced from cholesterol into estrogen (estradiol). Examples currently known to activate aromatase include vegetables selected from hydrangea tea, arnica, fennel, turmeric, corydalis tuber, *Trillium apetalon*, *Scutellaria baicalensis*, zedoary, yellow catalpa, immature orange, low bamboo (Kumazasa) schizonepeta spike, cassia seed, magnolia bark, evodia fruit, bupleurum root, Saisin (*Brassica rapa* var. *utilis*), Japanese pepper tree, cardamom, common mallow, Sinkyu (*cnidium officinale*), *Angelica acutiloba*. Kitag, tomato, *Glehnia littoralis*, atractylodes rhizome, dishcloth gourd, safflower, reedmace, lily, Japanese gentian, rosin, iris root, dead-nettle, *Ononis spinosa*, licorice, sophora root, grape fruit, cinnamon, Gentiana, Incense ware, condurango, salvia, hawthorn, dioscorea rhizome, bread, *Acorus calamus*, white birch, Japanese honeysuckle, *Crataegus oxyacantha* L., *Achillea millefolium*, mulberry root bark, thyme, cloves, citrus unshiu peel, spruce tree, tragacanth, *Hamamelis japonica*, bai zhi (Chinese name for angelica species *Angelica dahurica*), Butcher'S Broom, sinomenium stem, Imperatae Rhizoma, *Ledebouriella seseloides*, hop, ephedra herb, lavender, apple, lychee, lettuce, lemon, Roman chamomile, and burnet, extracts from these vegetables, yeast extracts, silk protein extracts, lactoprotein, trehalose, fermented soybeans extract, royal jelly, oryza oil, hydrolyzed wheat extract, shea butter, and fermented rice extract (Patent Documents 1 and 2).

CITATION LIST

Patent Document

Patent Document 1: JP 2005-343872 A
Patent Document 2: JP 2005-343873 A

SUMMARY OF THE INVENTION

Accordingly, in one embodiment, the present invention provides use of a compound represented by the formula (I) or a solvate thereof for producing an aromatase activator:

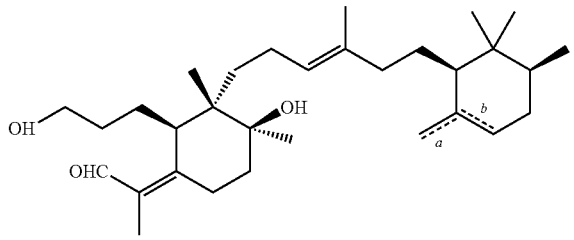

(I)

wherein the dashed line indicates that the bond may be a double bond, provided that a and b in the formula (I) do not simultaneously represent a double bond.

In another embodiment, the present invention provides use of a compound represented by the formula (I) or a solvate thereof for producing an agent for preventing and/or ameliorating estrogen deficiency disease or symptom.

In another embodiment, the present invention provides use of a compound represented by the formula (I) or a solvate thereof for producing a hair growth regulator.

In another embodiment, the present invention provides use of a compound represented by the formula (I) or a solvate thereof for producing a skin aging improver.

In another embodiment, the present invention provides use of a compound represented by the formula (I) or a solvate thereof for producing an external skin preparation.

In a further embodiment, the present invention provides an aromatase activation method comprising administering a compound represented by the formula (I) or a solvate thereof to a subject.

In still another embodiment, the present invention provides a method of preventing and/or ameliorating estrogen deficiency disease or symptom, the method comprising administering a compound represented by the formula (I) or a solvate thereof to a subject.

In still another embodiment, the present invention provides a hair growth regulating method comprising administering a compound represented by the formula (I) or a solvate thereof to a subject.

In still another embodiment, the present invention provides a skin aging improving method comprising administering a compound represented by the formula (I) or a solvate thereof to a subject.

DETAILED DESCRIPTION OF THE INVENTION

The term "non-therapeutic" as used herein is a concept excluding a medical action, that is, treatment action on human bodies by therapy.

The term "amelioration" as used herein means an improvement in disease or symptom, prevention or delay of aggravation of disease or symptom, or reverse, prevention, or delay of the progress of disease or symptom.

The term "prevention" as used herein means the prevention or delay of the onset of disease or symptom in individual bodies, or reduction in the risk of the onset of disease or symptom in individual bodies.

The term "skin aging" as used herein implies the states of the skin, for example, the reduction in the thickness of epidermis/dermis, reduction in the water content of the skin, disturbance of blood flow, reduction of collagen, reduction of elasticity, and increase of wrinkles.

The present invention relates to an aromatase activator which can promote the production of estrogen in a body safely by potentiating the activity of aromatase which is an enzyme biosynthesizing estrogen from androgen.

The inventors of the present invention have made studies concerning materials potentiating the activity of aromatase, and as a result, found a triterpene type compound having the effect of activating aromatase.

Because the aromatase activator of the present invention promotes the production of estrogen in a body and has high safety for human bodies, it is useful as medicines or cosmetics intended for preventing, ameliorating or treating various lesions caused by estrogen deficiency.

The aromatase activator of the present invention contains, as an active ingredient, a compound represented by the formula (I) or a solvate thereof:

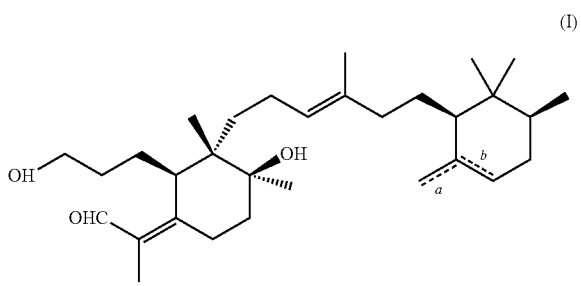

(I)

wherein the dashed line indicates that the bond may be a double bond, provided that a and b in the formula (I) do not simultaneously represent a double bond.

Examples of the solvate of the compound represented by the formula (I) include hydrates formed by absorbing water from the atmosphere or by recrystallization besides usual solvates (for example, hydrates) obtained by dissolving the compound represented by the formula (I) in a solvent.

The compound represented by the formula (I) has the effect of potentiating aromatase activity, as shown in Example below. Also, according to the compound of the formula (I) or its solvate, aromatase is activated, and thereby estrogen synthesis in a living body is promoted. The effects on the following diseases, symptoms, or states caused lay estrogen (Popular Medicine, No. 219, 2001, Nippon Hyoron Sha. Co., Ltd.; TAMASHA Teruhiko, Action of Female Hormone and Elicitation of Sexual Differences KINPODO, Inc., 2006) are therefore accomplished.

1) Action on Bone Metabolism:

The compound of the formula (I) or its solvate brings about retardation of the activity of a parathormone to thereby suppress bone resorption and also, promotes the activation of Vitamin D at the kidney to thereby suppress the progress of osteoporosis.

2) Action on Hyperlipidemia:

The compound of the formula (I) or its solvate prevents the occurrence of such a syndrome that reduction in the concentration of estrogen exacerbates the activity of LPL (lipoprotein lipase) activity, causing reduction in the number of LDL receptors and therefore causing the accumulation of LDL in the blood, leading to atherosclerotic state; increases the express ion of mRNAs in the vascular endothelium to exacerbate NO formation; and promotes the antioxidizing action and vasodilator action and acts in a suppressive manner on the progress of arteriosclerosis.

3) Action on a Cerebral Function:

The compound of the formula (I) or its solvate ameliorates cerebral functions such as remembrance, recognition function, and change in cerebral blood flow to affect feelings and emotion, and there is also a report concerning the relation to melancholy. In relation to, particularly, Alzheimer disease, the compound of the formula (I) or its solvate (i) acts on nerve cells to increase the activity of an Ach (acetylcholine) synthetic enzyme (choline acetyltransferase); (ii) stimulates the expression of, for example, receptors of a nerve growth factor (NGF) or brain-derived neurotrophic factor (BDNF) in the cholinergic neuron; (iii) increases synapse in the hippocampus; (iv) acts on an amyloid precursor protein (APP) to reduce the accumulation of β-amyloid, and thereby alleviating the damages to nerve cells; and (v) enhances intracerebral sugar transport and sugar assimilation.

4) Action on a Menopausal Disorder:

The compound of the formula (I) or its solvate ameliorates such a syndrome that the negative feedback operation in the hypothalamus-pituitary gland-ovary system is inhibited due to the reduction of estrogen and therefore, the hypothalamus and pituitary gland are put into a hyperenergetic state, that is, autonomic ataxia caused by the increase of LH (luteinizing hormone) and FSH (follicle-stimulating hormone).

5) Action on Eyes:

The compound of the formula (I) or its solvate suppresses the onset of macular degeneration and cataract which occur frequently in postmenopausal women. It also improves the lacrimal gland function to suppress dry eyes.

6) Action on Hair:

With regard to the hair of the head, the compound of the formula (I) or its solvate prolongs the growth period of the hair to promote the growth of the hair whereas, with regard to body hair, it depresses new hair growth to thereby reduce body hair density.

7) Effect on Beauty:

The compound of the formula (I) or its solvate ameliorates the conditions typified by reduction in the thickness of epidermis/dermis, reduction in the water content of the skin, disturbance of blood flow, reduction of collagen, reduction of elasticity, and increase of wrinkles.

Accordingly, the compound represented by the formula (I) or its solvate (hereinafter referred to as a compound of the formula (I) or the like) may be used as an active ingredient for the activation of aromatase, prevention and/or amelioration of estrogen deficiency disease or symptom in living bodies, regulation of hair growth, or amelioration of skin aging. This use may be those in humans or nonhuman animals, or tissues, organs, or cells derived from these humans and animals, and may be either therapeutic use or non-therapeutic use.

Examples of the above estrogen deficiency disease or symptom include osteoporosis, hyperlipidemia, cardiovascular disease such as arteriosclerosis, melancholy, memory disorder such as Alzheimer's disease, menopausal disorder, macular degeneration, cataract, and dry eyes, and preferably include the conditions typified by reduction in the thickness of epidermis/dermis, reduction in the water content of the skin, disturbance of blood flow, reduction of collagen, reduction of elasticity, and increase of wrinkles.

According to the present invention, an aromatase activator, an agent preventing and/or ameliorating estrogen deficiency disease or symptom, a hair growth regulator, and a skin aging improver, which each contain the compound of the formula (I) or the like as an active ingredient are provided. In an embodiment, these agents are respectively substantially constituted of the compound of the formula (I) or the like.

Also, according to the present invention, use of the compound of the formula (I) or the like for producing an aromatase activator, an agent for preventing and/or improving estrogen deficiency disease or symptom, a hair growth regulator, or a skin aging improver is provided.

Additionally, according to the present invention, use of the compound of the formula (I) or the like for producing an external skin preparation is provided.

In an embodiment, these agents are respectively constituted of the compound of the formula (I) or the like.

In another embodiment, the above estrogen deficiency disease or symptom is selected from the group consisting of osteoporosis, hyperlipidemia, arteriosclerosis, melancholy, memory disorder, Alzheimer's disease, menopausal disorder, macular degeneration, cataract, and dry eyes.

Also, in another embodiment, the above hair growth regulation is hair growth promotion or depression of new hair growth of body hair.

In still another embodiment, the above skin aging is selected from the group consisting of reduction in the thickness of epidermis or dermis, reduction in the water content of the skin, disturbance of blood flow, reduction of collagen, reduction of elasticity, and increase of wrinkles.

The effect of the above-described agent for preventing and/or ameliorating estrogen deficiency disease or symptom for preventing and/or ameliorating estrogen deficiency disease or symptom, the effect of the above-described hair growth regulator for regulating hair growth, and the effect of the above-described skin aging improver for ameliorating skin aging can be produced by aromatase activation.

The compound of the formula (I) or the like may also be used for producing compositions, medicines, quasi-drugs, cosmetics, and the like for aromatase activation, prevention and/or amelioration of estrogen deficiency disease or symptom, regulation of hair growth, or amelioration of skin aging.

The above compositions, medicines, quasi-drugs, cosmetics, and the like may be produced or used for humans or nonhuman animals. The compound of the formula (I) or the like may be an active ingredient which is formulated in the compositions, medicines, quasi-medicines, cosmetics, and the like and used for aromatase activation, prevention and/or amelioration of estrogen deficiency disease or symptom, regulation of hair growth, or amelioration of skin aging.

Such compositions, medicines, quasi-drugs, cosmetics, and the like are within the scope of the present invention.

The above medicines or quasi-drugs each contain the compound of the formula (I) or the like as an active ingredient. The above medicines or quasi-drugs may be administered in a desired dosage form. The administration may be performed orally or parenterally. Examples of dosage forms for oral administration include solid dosage forms such as a tablet, coating tablet, granule, powder, and capsule, and liquid dosage forms such as elixir, syrup, and suspension, and examples of dosage forms for parenteral administration include injection, transfusion, percutaneous administration, transmucosal administration, transnasal administration, enteric administration, inhalation, suppository, bolus, and patch.

The above medicines and quasi-drugs may respectively contain the compound of the formula (I) or the like either singly or in combination with pharmaceutically acceptable carriers. Examples of the carriers include an excipient, coating agent, binder, extender, disintegrating agent, lubricant, diluent, osmoregulating chemical, pH regulator, dispersant, emulsifier, antiseptic, stabilizer, antioxidant, colorants, ultraviolet absorber, humectants, thickener, activity enhancer, anti-inflammatory agent, disinfectant, perfume, taste masking agent, and odor improving agent. Also, the medicines and quasi-drugs may contain other active ingredients and pharmacological components insofar as the aromatase activation effect of the compound represented by the formula (I) is not lost.

The above medicine and quasi-drug can be produced by a usual method from the compound of the formula (I) or the like and depending on the need, by further combining the above carrier and/or other active ingredients and pharmacological components. The content of the compound of the formula (I) or the like in such medicines or quasi-drugs may be desired to be in a range from 0.0001 to 50% by mass, and is preferably from 0.001 to 10% by mass and more preferably from 0.01 to 1% by mass.

The above cosmetic contains the compound of the formula (I) or the like as active ingredients. The cosmetic may contain the compound of the formula (I) or the like either singly or in combination with a cosmetically acceptable carrier. Examples of the carrier include an excipient, coating agent, binder, extender, disintegrating agent, lubricant, diluent, osmoregulating chemical, pH regulator, dispersant, emulsifier, antiseptic, stabilizer, antioxidant, colorants, ultraviolet absorber, humectants, thickener, activity enhancer, anti-inflammatory agent, disinfectant, perfume, taste masking agent, and odor improving agent. Also, the cosmetic may contain other active ingredients and cosmetic components, for example, a humectant, whitening agent, ultraviolet protector, cell activating agent, detergent, keratolytic drug, and makeup components (for example, a makeup base, foundation, face powder, powder, cheek, rouge, eye makeup, eyebrow, mascara, and others), insofar as the aromatase activation effect of the compound represented by the formula (I) is not lost.

Examples of the form when the compound of the formula (I) or the like used for cosmetics include optional forms usable in cosmetics such as a cream, emulsion, lotion, suspension, gel, powder, pack, sheet, patch, stick, and cake.

The above cosmetic can be produced by a usual method from the compound of the formula (I) or the like and depending on the need, by further combining the above carrier and/or other active ingredients and cosmetic components. The content of the compound of the formula (I) or the like in the cosmetic may be in a range from 0.0001 to 50% by mass, and is preferably from 0.001 to 10% by mass and more preferably from 0.01 to 1% by mass based on the compound of the formula (I).

Also, the present invention provides an aromatase activating method in a subject. Such method includes a step of adding or administering the compound of the formula (I) or the like to a subject which has aromatase-expressing ability and in which aromatase is desired to be activated. Examples of the subject to be administered include tissues, organs, and cells derived from an animal, or their fractions, and animals which need aromatase activation. These animals are preferably humans or nonhuman mammals and more preferably humans.

In an embodiment, examples of the animals which need aromatase activation include animals affected with estrogen deficiency disease or symptom, animals suspected to be affected with these diseases or symptoms, or animals that are at risks of affection with these diseases or symptoms, animals that need hormone replacement therapy, or animals that need hair growth regulation or skin aging amelioration.

When the subject is culture cells, the above method is carried out by culturing these cells in the presence of the compound of the formula (I) or the like.

Also, according to the present invention, the compound of the formula (I) or the like can be administered in an effective amount to a subject that needs the compound or the like to prevent and/or ameliorate estrogen deficiency disease or symptom. Examples of the subject to be administered include animals affected with estrogen deficiency disease or symptom, animals suspected to be affected with the disease or symptom, or animals that are at risks of affection with the disease or symptom. These animals are preferably humans or nonhuman mammals and more preferably humans.

Also, according to the present invention, the compound of the formula (I) or the like can be administered in an effective amount to a subject that needs the compound or the like to regulate the hair growth of a living body.

Also, according to the present invention, the compound of the formula (I) or the like can be administered in an effective amount to a subject that needs the compound or the like to ameliorate the skin aging of a living body.

Examples of the subject to be administered include preferably humans or nonhuman mammals and more preferably humans. The administration of the compound or the like is performed non-therapeutically with the intention of hair growth regulation or amelioration of skin aging for improving beauty.

In an embodiment of the method of the present invention, the above estrogen deficiency disease or symptom is selected from the group consisting of osteoporosis, hyperlipidemia, arteriosclerosis, melancholy, memory disorder, Alzheimer's disease, menopausal disorder, macular degeneration, cataract, and dry eyes.

Also, in another embodiment, the above hair growth regulation is hair growth promotion of head or depression of new hair growth of body hair.

In another embodiment, the above skin aging is selected from the group consisting of reduction in the thickness of epidermis/dermis, reduction in the water content of the skin, disturbance of blood flow, reduction of collagen, reduction of elasticity, and increase of wrinkles.

In the method of the present invention, the concentration of the compound of the formula (I) or the like to be added or administered is from 0.00000001 to 1.0% (v/v), preferably from 0.0000001 to 0.1 (v/v), and more preferably from 0.000001 to 0.01% (v/v) in terms of final concentration in a culture product based on the compound of the formula (I) when the subject is culture cells. When the compound of the formula (I) or the like is administered to an adult, it is administered in a dose of from 0.000001 to 10000 mg/kg, preferably from 0.00001 to 1000 mg/kg, and more preferably from 0.0001 to 100 mg/kg per day based on the compound of the formula (I). In an embodiment, the compound of the formula (I) or the like may be administered percutaneously.

EXAMPLES

The present invention will be explained in more detail by way of examples.

Production Example 1

Preparation of Compounds 1 and 2

23 L of hexane was added to 2000 g of an iris root (orris root: Tochimoto Tenkaido Co., Ltd.) and extraction was carried out at ambient temperature for 5 days. The extraction liquid was concentrated under reduced pressure to obtain 25.7 g of an extract. This extract was fractionated by silica gel column chromatography (hexane:ethyl acetate=2:1→1:1→chloroform:methanol=7:1) to obtain 4.65 g of a fraction. This fraction was further subjected to fractionation with ODS column chromatography (methanol→ethanol→isopropyl alcohol) to obtain 1.21 g of a fraction. Next, 0.21 g of the fraction among 1.21 g of the obtained fraction was used to fractionate by ODS fractionation (water:acetonitrile=4:6→0:10) to collect 14.8 mg of a fraction. Next, ODS recycle fractionation (water:acetonitrile=15:85) was carried out to separate the fraction into each fraction of 94-min and 102-min peaks obtained by elution in 4th recycle. The fraction of 102-min peak was further subjected to ODS recycle fractionation (water:methanol=10:90) to collect the fraction of 71-min peak in 7th recycle, thereby obtaining 4.4 mg of a compound 1. Also, the fraction of 94-min peak was further subjected to ODS recycle fractionation (water:methanol=10:90) to collect the fraction of 52-min peak in 7th recycle, thereby obtaining 1.2 mg of a compound 2.

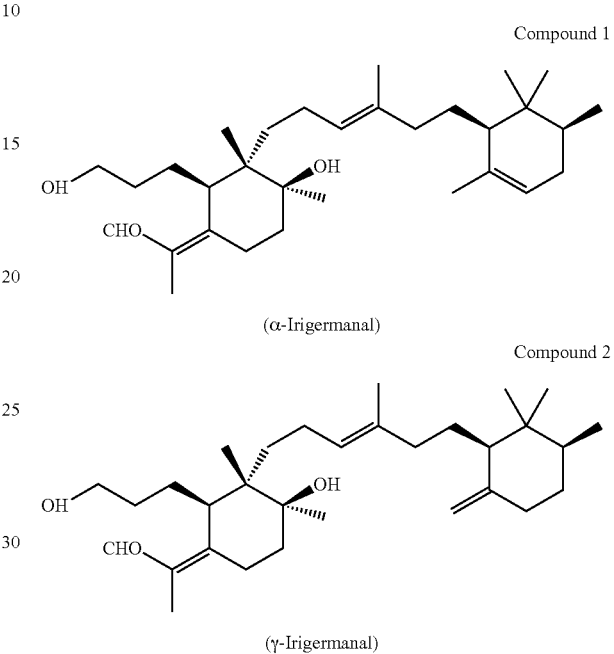

Compound 1

$^1$H-NMR (CDCl$_3$, δ ppm): 0.62 (s, 3H), 0.83 (d, J=6.7 Hz, 3H), 0.86 (s, 3H), 1.09 (s, 3H), 1.16 (s, 3H), 1.54 (s, 3H), 1.69 (s, 3H), 1.84 (br s, 3H), 1.0 to 2.2 (m, 20H), 2.58 (m, 2H), 3.31 (d, J=9.5 Hz, 1H), 3.60 (t, J=6.4 Hz, 2H), 4.98 (m, 1H), 5.31 (m, 1H), 10.2 (s, 1H)

Compound 2

$^1$H-NMR (CDCl$_3$, δ ppm): 0.52 (s, 3H), 0.82 (d, J=6.7 Hz, 3H), 0.94 (s, 3H), 1.09 (s, 3H), 1.17 (s, 3H), 1.52 (s, 3H), 1.84 (br s, 3H), 1.0 to 2.2 (m, 21H), 2.27 (m, 1H), 2.57 (m, 2H), 3.31 (d, J=9.5 Hz, 1H), 3.61 (t, J=6.4 Hz, 2H), 4.50 (br s, 1H), 4.81 (br s, 1H), 4.93 (t, J=7.0 Hz, 1H), 10.2 (s, 1H)

Test Example 1

Aromatase Activation Effect of the Compounds 1 and 2

The aromatase activation effect of the compounds 1 and 2 prepared in Production Example 1 was examined with reference to Stampfer M J, Willett W C, Colditz G A, Rosner B, Speizer F E and Hennenkens C H, N. Engl. J. Med., 313, 1044-1049, 1985.

Fibroblasts (HDF1616: KURABO) derived from human skin were planted in a 24-well cell culture plate (FALCON) to culture until it became confluent. The medium was removed and 900 μL of a serum-free medium was added to the wells to culture for 24 hr. At this time, the compound 1 or 2 prepared using an aqueous 95% ethanol solution such that the final concentration was $4.65 \times 10^{-6}$ mol/L was added to the wells. Also, a sample in which an aqueous 95% ethanol solution was added and a sample (no addition) in which no material was added were prepared as controls.

1β-3H-androst-4-ene-3,17-dione (Perkin Elmer) which was the substrate of aromatase was added in the serum-free medium such that the concentration was 37 kBq/100 μL and added in an amount of 100 μL in each well to culture for 24 hr. 900 μL of the culture product was taken, in a 2 mL tube from one well and 1 mL of $CHCl_3$ was added to the cultured product, which was then stirred vigorously. The cultured product was centrifuged at 15,000 rpm for 10 min to transfer the upper layer (water layer) to another tube. 200 μL of Charcoal/Dextran (which is one obtained by suspending 5 g of Charcoal, dextran coated (SIGMA) in 50 mL of $H_2O$) was added to the upper layer, which was fairly mixed and then allowed to stand at ambient temperature for 30 min. The mixture was centrifuged at 15,000 rpm for 10 min and the supernatant was transferred to a new tube. 1 mL of $HCl_3$ was added to the supernatant, which was then vigorously stirred and centrifuged at 15,000 rpm for 10 min and the upper layer (water layer) was added to 5 mL of Ultima Gold (Perkin Elmer) to measure the radioactivity of $^3H$ by a liquid scintillation counter (Perkin Elmer Tricarb 2550). The same serum-free medium containing no cell was incubated for the same hours without adding a drug, followed by the same procedures to measure the radioactivity of $^3H$ and the radioactivity was subtracted from the above measured radioactivity.

1β-3H-androst-4-ene-3,17-dione releases $^3H_2O$ by an aromatase reaction and is converted into estrogen having no radioactivity. In this experimental method, the radioactivity of released $^3H_2O$ is detected, showing that the higher the radioactivity is, the higher the aromatase activity is.

As shown in Table 1, the substrate was not almost decomposed in the case of the control (no addition) whereas high radioactivity based on the decomposition of aromatase substrate was obtained in all the cells to which the compounds 1 and 2 were respectively added, showing that the compounds 1 and 2 activated aromatase existing in cells.

TABLE 1

| Sample | Amount to be added (mol/L) | Aromatase activity (fmol/day/well) |
| --- | --- | --- |
| Compound 1 | 4.65 × 10⁻⁶ | 21.68 |
| Compound 2 | 4.65 × 10⁻⁶ | 22.34 |
| Control | | 6.85 |

The invention claimed is:

1. A method of treating an estrogen deficiency disease or symptom, the method comprising administering a compound represented by the following formula (I) or a solvate thereof to a subject in need thereof:

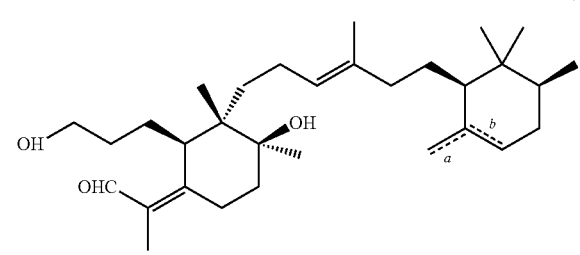

(I)

wherein the dashed line indicates that the bond may be a double bond, provided that a and b in the formula (I) do not simultaneously represent a double bond.

2. The method according to claim 1, wherein the estrogen deficiency disease or symptom is selected from the group consisting of osteoporosis, hyperlipidemia, arteriosclerosis, melancholy, memory disorder, Alzheimer's disease, menopausal disorder, macular degeneration, cataract, and dry eyes.

3. The method of treating estrogen deficiency disease or symptom according to claim 1, wherein the subject is an adult and the daily dosage of the compound represented by the formula (I) or the solvate thereof is from 0.000001 to 10000 mg/kg.

4. The method of treating estrogen deficiency disease or symptom according to claim 3, wherein the subject is an adult and the daily dosage of the compound represented by the formula (I) or a solvate thereof is from 0.00001 to 1000 mg/kg.

5. The method of treating estrogen deficiency disease or symptom according to claim 4, wherein the subject is an adult and the daily dosage of the compound represented by the formula (I) or the solvate thereof is from 0.0001 to 100 mg/kg.

6. A hair growth regulating method comprising administering a compound represented by the following formula (I) or a solvate thereof to a subject in need thereof:

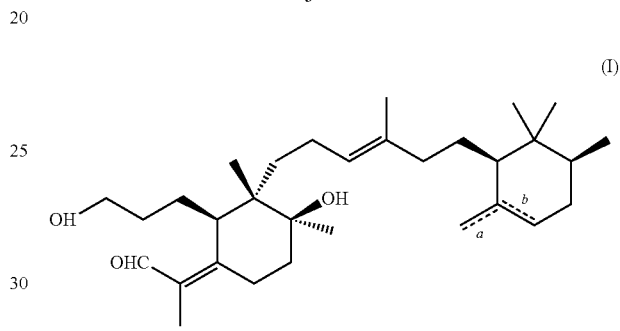

(I)

wherein the dashed line indicates that the bond may be a double bond, provided that a and b in the formula (I) do not simultaneously represent a double bond.

7. The hair growth regulating method according to claim 6, wherein the subject is an adult and the daily dosage of the compound represented by the formula (I) or the solvate thereof is from 0.000001 to 10000 mg/kg.

8. The hair growth regulating method according to claim 7, wherein the subject is an adult and the daily dosage of the compound represented by the formula (I) or the solvate thereof is from 0.00001 to 1000 mg/kg.

9. The hair growth regulating method according to claim 8, wherein the subject is an adult and the daily dosage of the compound represented by the formula (I) or the solvate thereof is from 0.0001 to 100 mg/kg.

10. A skin aging improving method comprising administering a compound represented by the following formula (I) or a solvate thereof to a subject in need thereof:

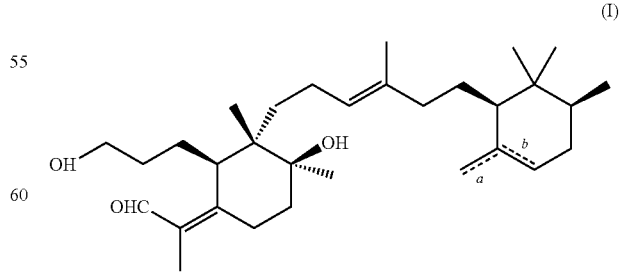

(I)

wherein the dashed line indicates that the bond may be a double bond, provided that a and b in the formula (I) do not simultaneously represent a double bond.

11. The method according to claim 10, wherein the skin aging is selected from the group consisting of reduction in the thickness of epidermis/dermis, reduction in the water content of the skin, disturbance of blood flow, reduction of collagen, reduction of elasticity, and increase of wrinkles.

12. The skin aging improving method according to claim 10, wherein the subject is an adult and the daily dosage of the compound represented by the formula (I) or the solvate thereof is from 0.000001 to 10000 mg/kg.

13. The skin aging improving method according to claim 12, wherein the subject is an adult and the daily dosage of the compound represented by the formula (I) or the solvate thereof is from 0.00001 to 1000 mg/kg.

14. The skin aging improving method according to claim 13, wherein the subject is an adult and the daily dosage of the compound represented by the formula (I) or the solvate thereof is from 0.0001 to 100 mg/kg.

* * * * *